United States Patent [19]

Ellison et al.

[11] Patent Number: 4,570,623
[45] Date of Patent: Feb. 18, 1986

[54] ARCHED BRIDGE STAPLE

[75] Inventors: Arthur E. Ellison, Williamstown, Mass.; Rocco R. Borzone, Emerson, N.J.

[73] Assignee: Pfizer Hospital Products Group Inc., New York, N.Y.

[21] Appl. No.: 500,506

[22] Filed: Jun. 2, 1983

[51] Int. Cl.$^4$ .............................................. A61F 5/04
[52] U.S. Cl. ............................ 128/92 B; 128/334 R; 128/337
[58] Field of Search ............ 128/92 B, 334 R, 334 C, 128/92 R, 92 EC, 92 ED

[56] References Cited

U.S. PATENT DOCUMENTS 4,263,903  4/1981  Griggs .............................. 128/92 B
4,438,769  3/1984  Pratt et al. ......................... 128/334
4,454,875  6/1984  Pratt et al. ....................... 128/334 R

OTHER PUBLICATIONS

From Bickham's "Operative Surgery" 1924, pp. 368, 369.
Journal of Bone & Joint Surgery "Boat-Nail Fixation of Tendons & Ligaments to Cancellous Bone" Augustine et al., Oct. 1956, vol. 38A, No. 5, pp. 1156-1158.
Richards Mfg. Co., Memphis Tenn. Orthopedic Catalog 1975, p. 72, M. Stone Table Staples.

Primary Examiner—Gene Mancene
Assistant Examiner—C. W. Shedd
Attorney, Agent, or Firm—Charles J. Knuth; Peter C. Richardson; Lorraine M. Donaldson

[57] ABSTRACT

A bone staple for attaching tubular shaped soft tissue to bone, in which the transverse bridge of the staple has teeth on its underside to grip the tissue and is arch shaped so that the center of the bridge is above the bone surface when the staple legs are driven fully into a bone.

7 Claims, 5 Drawing Figures

ARCHED BRIDGE STAPLE

BACKGROUND OF THE INVENTION

This invention relates to the field of surgical bone staples, and more specifically to staples for securing soft tissue to bone.

It often becomes necessary in the surgical art to reapply soft tissue (e.g., ligaments, muscles, cartilage and tendons) to the bone structure of a patient so as to cause adherence and growth of the soft tissue to the bone. Thus, for example, soft tissue torn loose from the underlying bone in an injury is so rejoined. In other operations, soft tissue is surgically separated from the underlying bone so that it can be shortened or moved, and is then rejoined to the bone. An example of such an operation is the well known surgical procedure in which the patellar tendon is translated medially to inhibit lateral subluxation of the patella in the femoral groove.

Surgical staples provided with soft-tissue retaining teeth on the underside on the transverse bridge member are known. An example of such a staple is the Richards fixation staple (Richards Manufacturing Co., Inc.; Memphis, Tenn.). Another example is the DePalma Staple (Howmedica, Inc.; Rutherford, N.J.). Also U.S. Pat. No. 4,278,091 discloses a combination bone staple and tissue retention element having a multiplicity of teeth on its underside. In all these staples, the bridge of the staple is either straight or curved slightly to conform generally to the expected arc of the bone, and the teeth are short. Therefore, when these prior art staples are used to secure tubular or elliptical shaped soft tissue to a bone, the tissue is squeezed flat between the bridge and bone surface. The pressure causing this distortion of tubular tissue can produce serious injury to that tissue and retard its desired healing and adherence to the bone.

SUMMARY OF THE INVENTION

It is the object of the present invention to provide a bone staple which will attach tubular soft tissue to bone securely, but without unnecessary compressive injury of that tissue.

This objective and other advantages are achieved by a bone staple in which the bridge member is arched above the bone surface when in place. This design minimizes possible injury to tublar tissue by excessive pressure between bridge and bone. The concave underside of the arched bridge has a plurality of depending teeth to pierce and hold the tissue securely at the site of attachment.

DETAILED DESCRIPTION OF THE PREFERRED EMBODIMENT

Figure 1:
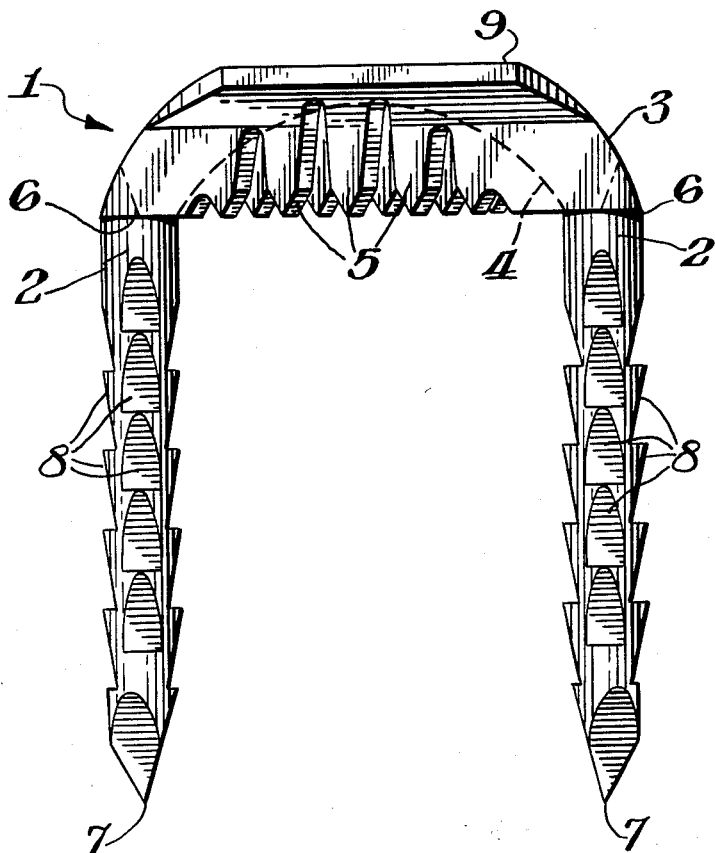
FIG. 1 is an elevation front view of a staple according to this invention.

The invention will be described in terms of the preferred embodiment of a bone staple according to this invention. This preferred embodiment is shown in FIG. 1. This staple 1 has two generally parallel legs 2, joined at their upper ends by a transverse bridge member 3. The bridge member 3 is in the form of an arch coplanar with the legs 2. The concave surface 4 of the arch 3 faces legs. The bridge member joins the legs in a plane perpendicular to the legs. However, if desired, for special uses, the bridge member can join the legs in a plane oblique to the legs, as in an angulated staple.

Figure 2:
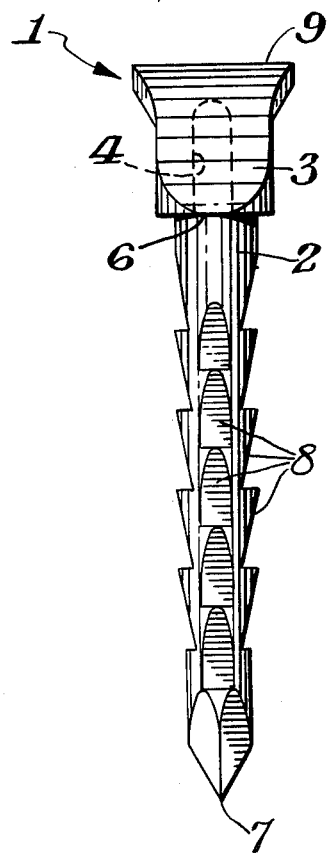
FIG. 2 is an elevation side view of the FIG. 1 staple.

The bridge member 3 is wider (in the direction normal to the plant of FIG. 1) than the legs 2 as shown at their juncture 6 in FIG. 2, and has an even wider flattened center section to provide an impact head 9 for driving the staple into a bone.

The legs 2 taper slightly from their upper ends at the juncture 6 with the bridge member 3 to their lower ends 7. The lower ends 7 are sharply pointed. The sides of the legs are serrated with the points 8 of the serrations directed away from the pointed lower ends 7 of the legs.

Figure 3:
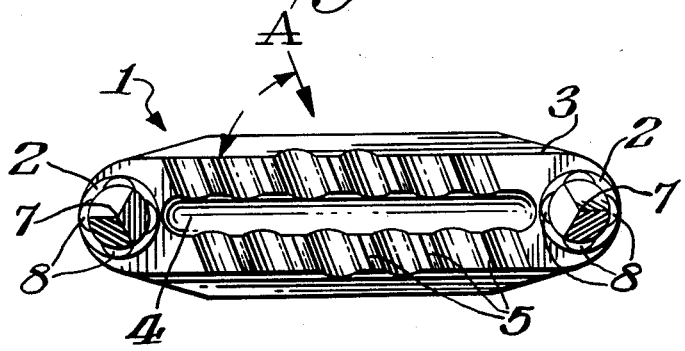
FIG. 3 is a bottom view of the FIG. 1 staple.
Figure 4:
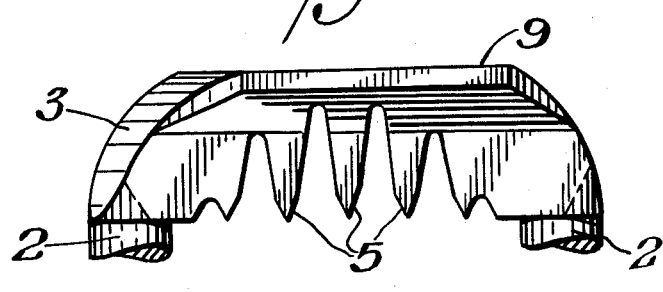
FIG. 4 is an oblique partial view of a staple bridge viewed in the direction of arrow A in FIG. 3.

The concave surface 4 of the bridge member 3 has a plurality of pointed teeth 5 depending from it. These teeth are generally parallel to the legs, and vary in length so that their points essentially form a plane normal to the legs at the juncture 6 of the legs with the bridge member. In this preferred form of staple, the teeth 5 are arranged in two rows depending from the sides of the concave surface 4 of bridge member 3. They are created by milling intersecting grooves in the bridge member. A parallel set of these grooves is milled at an oblique angle to an arc-shaped groove milled parallel to the plane of the staple so that two rows of teeth are created with the teeth in one row offset from those in the other row. Thus, the teeth will have parallelogram cross sections. In this method of manufacture, the arc-shaped groove creates the concave surface 4 of bridge member 3. This is shown in FIGS. 1, 3 and 4. The ends of the teeth are sharply tapered to a point.

This staple is typically used as follows: a strip of soft tissue with a tubular or elliptical cross section (e.g., tendon, ligament, muscle, cartilage) is positioned against a bone where it is to be rejoined. The staple is placed with one leg on either side of the strip, generally straight across from one another, and driven into the bone. In cases of very hard bone, pilot holes may have to be drilled to ease entrance of the staple legs into the bone. As the legs are driven fully into the bone, the bridge member will press the tissue down and the teeth pierce through it to the bone surface forming a secure attachment. The attachment is secure because the bridge member prevents upward movement, the teeth hold against lengthwise movement and the legs prevent any sideways movement. This secure attachment is achieved with minimum risk of damage to the tissue or its vascularity by excessive compression under the bridge member, as can happen with conventional toothed staples, because the bridge member is arched up off the surface of the bone. It cannot be forced too far into the tissue even though the legs are driven as far as possible into the bone. The staple can be used in this same way to attach artificial tissues, such as artificial tendons and ligaments.

The staples of this invention can be made in a range of sizes for use with bones and tissues of different diameter and thickness. A typical staple has legs 22.9 mm long, 3.0 mm diameter, and held 15.5 mm apart by the arched bridge member. The concave surface of the bridge member rises 4.3 mm over its juncture with the legs. The impact head is 6.1 mm above that juncture. Since the teeth depend from the concave underside of the bridge and end at the plane of the leg-bridge juncture, they are of various lengths. In this embodiment, there are five teeth in each of two rows varying from a maximum length of 4.3 mm at the center to a practical minimum of about 1.3 mm at the sides.

Figure 5:
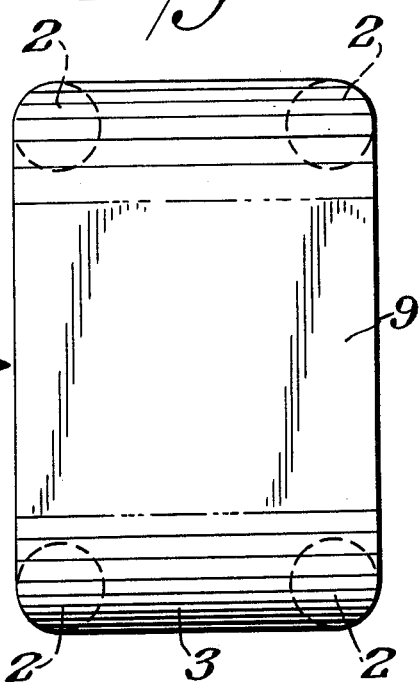
FIG. 5 is a top view of another staple according to this invention.

The presently preferred staple has two legs as described above. However, the scope of the invention is not limited to that embodiment. A staple according to this invention can have a plurality of legs. For example, a "table staple" having four legs in a rectangular pattern can be made. In one staple of this type, a top plan view would be as shown in FIG. 5. An elevation view of the side through which tubular tissue would pass (arrow B in FIG. 5) would be similar to FIG. 1.

In FIG. 5, the bridge joins four legs 2 (shown in dotted outline), one leg in each corner. The bridge 3 is approximately as wide (direction of arrow B) as is its arch span. Where the bridge arch is circular, the bridge will be in the form of a cylindrical section with its axis parrallel to arrow B. A rectangular flattened section is centered on top of the bridge to provide an impact head 9.

While the invention is not limited to any particular set of staple dimensions or size and arrangement of teeth, it is important that the center of the bridge be arched high enough so that its concave underside remains significantly above the bone surface when the legs are fully driven in. This is achieved in most cases when the arch in the bridge member has a rise in the range of about 20 percent to about 50 percent of the staple span. In the typical staple described above, the arch rise is (4.3/15.5)×100=27.7 percent of the span.

We claim:

1. A surgical bone staple comprising,
a bridge member joined at each end to a pointed leg having a longitudinal axis, the legs pointing in the same general direction and being in a plane substantially coplanar with said bridge member,
said bridge member being in the form of an arch when viewed both in said plane and perpendicular to said plane, having its concave surface facing said legs, the outer surface of the bridge member having a flattened planar section, substantially perpendicular to said longitudinal axes, which forms an impact head for driving the staple into a bone;
a plurality of pointed teeth depending from said concave surface and generally parallel to said legs, and teeth being substantially shorter than said legs, wherein the points of the teeth lie essentially in a plane substantially perpendicular to the legs at their upper ends, and
said arch having a rise of about 20% to about 50% of its span, whereby the center of said concave surface remains substantially spaced above a bone surface when said legs are driven fully into said bone.

2. A surgical bone staple as in claim 1 wherein the teeth are arranged in two rows extending along the concave surface of the bridge member.

3. A surgical bone staple as in claim 2 wherein the teeth in one row are offset from those in the other row.

4. A surgical bone staple as in claim 3 wherein the teeth have cross sections in the form of parallelograms with a first pair of sides parallel to the plane of said bridge member and a second pair of sides oblique to said first sides.

5. A surgical bone staple as in claim 1 wherein the legs are tapered from their upper to their lower ends.

6. A surgical bone staple as in claim 5 wherein the legs are serrated with the serration points directed away from the lower ends of the legs.

7. A surgical bone staple as in claim 1 in which the rise of the arch in the bridge member is about 28% of the span of the staple.

* * * * *